US012685282B1

(12) United States Patent　　　　(10) Patent No.:　US 12,685,282 B1
Gault et al.　　　　　　　　　　　(45) Date of Patent:　　Jul. 21, 2026

(54) SOYBEAN VARIETY SENF2101

(71) Applicant: INARI AGRICULTURE TECHNOLOGY, INC., Cambridge, MA (US)

(72) Inventors: Christine Marie Gault, Cambridge, MA (US); Rodrigo German Sala, Wildwood, MO (US)

(73) Assignee: Inari Agriculture Technology, Inc., Cambridge, MA (US)

( * ) Notice: Subject to any disclaimer, the term of this patent is extended or adjusted under 35 U.S.C. 154(b) by 233 days.

(21) Appl. No.: 18/186,309

(22) Filed: Mar. 20, 2023

Related U.S. Application Data

(60) Provisional application No. 63/269,670, filed on Mar. 21, 2022.

(51) Int. Cl.
　　*A01H 6/54*　　　　(2018.01)
　　*A01H 5/10*　　　　(2018.01)
(52) U.S. Cl.
　　CPC .............. *A01H 6/542* (2018.05); *A01H 5/10* (2013.01)
(58) Field of Classification Search
　　None
　　See application file for complete search history.

(56) References Cited

U.S. PATENT DOCUMENTS

| | | | | |
|---|---|---|---|---|
| 9,609,831 | B1 * | 4/2017 | Eby .................... | C12N 15/8241 |
| 2023/0279410 | A1 | 9/2023 | Shalitin et al. | |

FOREIGN PATENT DOCUMENTS

| | | |
|---|---|---|
| WO | 2021186433 A1 | 9/2021 |
| WO | WO 2023/183772 | 9/2023 |

OTHER PUBLICATIONS

Cai et al., "CRISPR/Cas9-mediated gene editing of GmJAGGED1 increased yield in the low-latitude soybean variety Huachun 6," Plant Biotechnology Journal, 2021, vol. 19, pp. 1898-1900.
Cermak et al., "A Multipurpose Toolkit to Enable Advanced Genome Engineering in Plants," The Plant Cell, Jun. 2017, vol. 29, pp. 1196-1217.
Hood et al., "New Agrobacterium helper plasmids for gene transfer to plants," Transgenic Research, 1993, vol. 2, pp. 208-218.
Jeong et al., "Ln Is a Key Regulator of Leaflet Shape and Number of Seeds per Pod in Soybean," The Plant Cell, Dec. 2012, vol. 24, pp. 4807-4818.
Kaeppler et al., "Epigenetic aspects of somaclonal variation in plants," Plant Molecular Biology, 2000, vol. 43, pp. 179-188.
Li et al., "Optimization of Agrobacterium-Mediated Transformation in Soybean," Frontiers in Plant Science, Feb. 2017, vol. 8, No. 246, 15 pages.
Liu et al., "The Soybean Stem Growth Habit Gene Dt1 Is an Ortholog of *Arabidopsis* Terminal Flower," Plant Physiology, May 2010, vol. 153, pp. 198-210.
Pareddy et al., "Improved soybean transformation for efficient and high throughput transgenic production," Transgenic Res, 2020, vol. 29, pp. 267-281.
Sayama et al., "Confirmation of the pleiotropic control of leaflet shape and number of seeds per pod by the Ln gene in inducted soybean mutants," Breeding Science, 2017, vol. 67, pp. 363-369.
Stroud et al., "Plants regenerated from tissue culture contain stable epigenome changes in rice," elife, 2013, vol. 2, 14 pages.
Tsuda et al., "Construction of a high-density mutant library in soybean and development of a mutant retrieval method using amplicon sequencing," BMC Genomics, 2015, vol. 16, No. 1014, 18 pages.
Dinkins et al., "Expression of the Narrow Leaflet Gene for Yield and Agronomic Traits in Soybean," The Journal of Heredity, 2002, vol. 93, No. 5, pp. 346-351.

* cited by examiner

*Primary Examiner* — Vinod Kumar
(74) *Attorney, Agent, or Firm* — Klarquist Sparkman, LLP

(57)　　　　　　ABSTRACT

Seed, plants, plant parts, and plant cells of soybean variety SENF2101 are disclosed. This variety was developed with a cutting-edge multiplex gene editing platform. Leveraging natural genetic diversity, this variety seeks to generate increased yields while also reducing the environmental footprint of soybeans as a significant step towards nature positive farming for a healthy planet and people.

20 Claims, No Drawings

SOYBEAN VARIETY SENF2101

CROSS REFERENCE TO RELATED APPLICATIONS

This application claims priority under 35 U.S.C. § 119 to provisional patent application U.S. Ser. No. 63/269,670 filed Mar. 21, 2022. The provisional patent application is herein incorporated by reference in its entirety, including without limitation, the specification, claims, and abstract, as well as any figures, tables, appendices, or drawings thereof.

BACKGROUND

Soybean is an important crop globally due to its ability to fix atmospheric nitrogen in the soil while serving as a major source of animal feed protein and soybean oil for food, industrial and biodiesel use. Soybean farmers work hard to help ensure shelves are stocked and families are fed around the world.

Farming to preserve soil, water and nutrient resources for future generations is a priority for U.S. farmers, breeders and policymakers. Unprecedented changes in farming technologies and methods in the 20th century provided food, feed and fuel to a rapidly growing world population. In the 21st century, necessity to improve soil nutrition, biodiversity and carbon sequestration, water use and pollution levels, nitrogen and phosphorus management, and land conservation drives further opportunity for advancement.

Crop gene editing has once-in-a-century potential to leverage natural plant diversity and to deliver high yielding crops that are locally adapted, more resilient and a cornerstone in nature positive farming for healthy soil, water, atmosphere, plants, animals and humans. Decades of commodity crop inbreeding to achieve commercially elite, high yielding cultivars has limited genetic diversity resulting in vulnerability to environmental degradation and climate changes' abiotic and biotic stressors. Higher yield crops achieved through greater genetic diversity will, on a per bushel basis, reduce land, fertilizer and water needs and thus reduce on-farm and supply chain greenhouse gas emissions, along with water, soil and air pollution. Gene editing will also generate plants with greater resistance to pests and diseases, hardiness during extreme weather events, and reduced water and fertilizer needs. Because of this, gene edited seeds are poised to become a foundation for sustainable farming systems that support robust ecosystems and value chains.

The instant soybean variety seeks to meet these needs.

SUMMARY

One aspect of the disclosure is a seed, plant, plant part, or plant cell of soybean variety SENF2101. In an aspect of the disclosure, the seed, plant, plant part, or plant cell of soybean variety SENF2101 is free of transgenic, genetically modified events.

Another aspect of the disclosure is a method to produce a soybean seed by harvesting soybean seed from a cross of two soybean plants, where at least one soybean plant is the soybean plant SENF2101. A further aspect of the disclosure is an F1 soybean seed produced by this method.

Another aspect of the disclosure is a method to develop a second soybean plant by applying a plant breeding technique or a breeding tool to a soybean plant grown from F1 seed produced from a cross of soybean plant SENF2101 and another, different soybean plant, where application of the technique results in development of the second soybean plant.

Another aspect of the disclosure is a method to produce a soybean plant derived from variety SENF2101 by: a) crossing soybean plant variety SENF2101 with itself or a second plant to produce progeny seed; b) growing the progeny seed to produce a progeny plant and crossing the progeny plant with itself or a different plant to produce further progeny seed; and, c) repeating step (b) for at least one additional generation to produce a soybean plant derived from the variety SENF2101.

Another aspect of the disclosure is a method to isolate nucleic acids from seed, plant, plant part, or plant cell of soybean variety SENF2101. A further aspect is a method to analyze the nucleic acids to produce data and recording the data for soybean variety SENF2101. In one more aspect, the data is recorded on a computer readable medium.

Another aspect of the disclosure is a method to edit the genome of soybean variety SENF2101 by editing the genome of its seed, plant, plant part, or plant cell, where the gene editing method is selected from the group selected from the group consisting of zinc finger nucleases, transcription activator-like effector nucleases (TALENs), engineered homing endonucleases/meganucleases, and clustered regularly interspaced short palindromic repeat (CRISPR)-associated protein systems. A further aspect of the disclosure is a soybean seed or plant produced by this method.

Another aspect of the disclosure is a soybean plant expressing all the physiological and morphological characteristics of soybean plant variety SENF2101.

Another aspect of the disclosure is a method to generate a molecular marker profile from nucleic acids isolated from the seed, plant, plant part, or plant cell of soybean variety SENF2101.

Another aspect of the disclosure is a method to produce a soybean seed or plant including a locus conversion by introducing the locus conversion into soybean plant variety SENF2101 or its seed. A further aspect of the disclosure is a converted seed, plant, plant part or plant cell of soybean variety SENF2101, where the converted seed, plant, plant part or plant cell includes a single locus conversion, and where the plant or a plant grown from the converted seed, plant part or plant cell includes the locus conversion and otherwise has the same morphological and physiological characteristics of soybean variety SENF2101 when grown under the same environmental conditions.

A further aspect of the disclosure is the converted seed, plant, plant part or plant cell, where the single locus conversion confers a trait selected from the group consisting of male sterility, increased yield, a site-specific recombination site, abiotic stress tolerance, altered phosphate, altered antioxidants, altered fatty acids, altered essential amino acids, altered carbohydrates, herbicide resistance, insect resistance and disease resistance. A further aspect of the disclosure is the converted seed, plant, plant part or plant cell, where the locus conversion is introduced by backcrossing or transformation.

Another aspect of the disclosure is a method to produce treated seed by applying a seed treatment to the seed of soybean variety SENF2101. A further aspect of the disclosure is a treated soybean seed produced by this method.

Another aspect of the disclosure is a soybean commodity plant or seed produced from the plant or seed of soybean variety SENF2101, where the commodity plant product includes as least one cell of soybean variety SENF2101.

Another aspect of the disclosure is the seed of soybean variety SENF2101 having a decreased seed weight phenotype.

DETAILED DESCRIPTION

"Backcrossing" refers to a process in which a breeder crosses a donor parent variety possessing a desired trait or traits to a recurrent parent variety (e.g., a recurrent parent that is agronomically superior but lacks the desired level or presence of one or more traits) and then crosses the resultant progeny back to the recurrent parent one or more times. Backcrossing can be used to introduce one or more desired traits from one genetic background into another background that is lacking the one or more desired traits.

"Breeding" refers to genetic manipulation of soybean varieties, including application of one or more agricultural and/or biotechnological tools, methods and/or processes to create useful new distinct varieties.

"Cell" refers to a soybean plant cell, whether isolated, in tissue culture, or incorporated in a plant or plant part. The soybean plant cell can be a cell, such as a somatic cell of the variety having the same set of chromosomes as the cells of the seed of the variety, or a cell that contains an edited genome or a locus conversion or transgene otherwise having the same or essentially the same set of chromosomes as the cells of the seed of the variety.

"Crossing" refers to fertilization by the union of two games from different soybean plants, such as by cross-pollinating. Crossing refers to a simple x by y cross or backcrossing, depending on context.

"Elite variety" refers to a soybean variety that is sufficiently homozygous and homogenous to be used for commercial grain production. An elite variety may also be used as source germplasm in further breeding.

"Flower color" refers to the color of the flower petals. Data values include white and purple.

"Gene editing" refers to technologies used to precisely change the DNA in a soybean plant. Possible changes include, but are not limited to, mutating an allele, increasing or decreasing the expression of an allele, or adding or removing an allele. Generally, these genomic changes are enabled through the use of various nucleases, and the genes or alleles changed are of the plant species being altered as opposed to adding alleles or genes from a different species. Gene editing also allow the simultaneous gene-editing of multiple alleles during the same or a separate procedure. Gene-editing is another breeding tool for adding genetic diversity; an important basis for heterosis and higher plant performance.

"Genetically modified herbicide resistance events" refers to presence of genetically modified events in the tested soybean variety. "None" indicates that, at a minimum, wild-type plants tested negative for presence of 40-3-2, MON87708, MON89788, and Pat.

"Hilum color" refers to the color of the scar left on the soybean seed that marks the place where the seed was attached to the pod before harvest. Data values include: buff, yellow, brown, gray, imperfect black, and black.

"Leaflet shape" is the shape of the leaflets at middle canopy. Data values include: linear, lanceolate, oval, ovate, and cordate.

"Locus" refers to a defined segment of DNA.

"Locus conversion" refers to seeds, plants, and/or parts thereof developed by backcrossing, introgression or genetic transformation where essentially all of the desired morphological and physiological characteristics of a variety are recovered in addition to at least one locus that has been transferred into the variety by introgression, backcrossing, or transformation. The locus can be a native locus, a transgenic locus, or a combination thereof.

"Mature" refers to soybean plants that are physiologically mature. This occurs when 95% of the pods have reached their mature color.

"Maturity group" refers to an agreed-on industry division of groups of soybean varieties, based on the zones that they are adapted, primarily according to day length or latitude. They consist of very long day length varieties (Groups 000, 00, 0) and extend to very short day length varieties (Groups VII, VIII, IX, X).

"Nucleic acid" refers to an acidic, chain-like biological macromolecule consisting of multiple repeat units of phosphoric acid, sugar, and purine and pyrimidine bases. Nucleic acids include single stranded or double stranded nucleic acids, as specified, or contain portions of both double stranded or single stranded sequence. Nucleic acids include DNA (including genomic and cDNA), RNA (including mRNA and rRNA) or a hybrid, where the nucleic acid contains any combination of deoxyribo- and ribo-nucleotides, and any combination of bases.

"Plant" includes reference to an immature or mature whole soybean plant, including a plant from which seed or grain or anthers have been removed. Any seed or embryo that will produce the plant is also considered to be the soybean plant.

"Plant habit" refers to the physical appearance of a soybean plant. Indeterminate varieties are those in which stem growth is not limited by formation of a reproductive structure (i.e., flowers, pods and seeds) and hence growth continues throughout flowering and during part of pod filing. The main stem develops and sets pods over a prolonged period under favorable conditions. Determinate varieties are those in which stem growth ceases at flowering time. Most flowers develop simultaneously, and most pods fill at approximately the same time. Semi-determinate describes plant habit for plants showing stem termination intermediate between that of determinate and indeterminate. Data values include: determinate, semi-determinate, and indeterminate.

"Plant height" refers to plant height taken from top of the soil to the uppermost node of the plant at maturity and is measured in cm.

"Plant lodging" is the tendency of a soybean plant to lodge, measured at maturity. A score of 1 indicates no lodging or leaning plants, a score of 3 indicates less than 10% plants leaning with majority still straight for easy combining, a score of 5 indicates greater than 30% plants lodging with some plants leaning significantly, a score of 7 indicates about 50% plants significantly leaning over with impact on ease of combining, and a score of 9 indicates greater or equal to 70% plants leaning significantly.

"Plant part" includes a leaf, stem, root, root tip, anther, seed, grain, embryo, pollen, ovule, flower, cotyledon, hypocotyl, node, pod, flower, pistil, petiole, petal, shoot, stalk, tissue, protoplast, tissue culture, callus, clump, cell and the like. A plant part includes at least one cell, such as a somatic cell or a meristematic cell, of the soybean plant from which the plant part was obtained.

"Pod color" refers to the color of the pod walls of mature soybean plants. The pod consists of the hull or shell (pericarp) and the soybean seeds. Pod color data values include: brown and tan.

"Pods per plant" refers to the number of pods present on mature plants.

"Pubescence color" refers to the color of the covering of very fine hairs closely arranged on the leaves, stems and pods of the soybean plant. Data values include: gray, brown, tawny, and light tawny.

"Relative maturity" refers to soybean maturities that are divided into maturity groups (denoted as 000, 00, 0, I, II, III, IV, V, VI, VII, VIII, IX, X, or 000, 00, 0, 1, 2, 3, 4, 5, 6, 7, 8, 9, 10). Within a maturity group are sub-groups. A sub-group is a tenth of a maturity group (for example 1.3 would indicate a group 1 and subgroup 3). Within narrow comparisons, the difference of a tenth of a relative maturity group equates very roughly to a day difference in maturity at harvest.

"Seed coat color" is seed coat color of mature plants. Data values include yellow, green, brown, and black.

"Seed coat luster" refers to seed coat bloom, i.e., a coating of powdery substance adhering to the mature seed coat. Data values include dull (trace bloom), bloom, intermediate (between dull and shiny), and shiny (absence of bloom).

"Seed oil content" refers to the percent of total seed weight of a soybean seed that is composed of oils.

"Seed protein content" refers to the percent of total seed weight of a soybean seed that is composed of protein.

"Seed size distribution" refers to the seed size distribution determined by using round-hole screens ranging from 10/64 inches to 22/64 inches in diameter. Data values include N=seed size distribution of claimed variety did not substantially vary from seed size distribution of comparison variety, and Y=seed size distribution of claimed variety did substantially vary from seed size distribution of comparison variety.

"Seeds per plant" refers to the number of seeds harvested from single plants as calculated by plot.

"Seeds per pod" refers to the number of soybean seeds per pod from single plants.

"Seeds per pound" is the number of soybean seeds per pound.

"Seed yield" is the dry yield in bushels/acre of the grain at harvest.

"Shattering" refers to the amount of pod dehiscence before harvest. Pod dehiscence involves seeds falling from the pods to the soil. This is a visual score from 1 to 9 comparing all genotypes within a given test. A score of 1 indicates pods have not opened and no seeds have fallen out, a score of 3 indicates about 30% of the plants have pods open, a score of 5 indicates about 50% of the plants have pods open, a score of 7 indicates about 75% of the plants have pods open, and a score of 9 indicates at least 90% of the pods are open.

"Single Locus Converted (Conversion) Plant" refers to soybean plants that are developed by a plant breeding technique called backcrossing, in which essentially all of the morphological and physiological characteristics of a soybean variety are recovered in addition to the characteristics of the locus transferred into the variety via the backcrossing technique. Once introduced into any soybean plant genome, a locus that is transgenic in origin (transgene), can be introduced by backcrossing as with any other locus.

"Treated seed" means seed of variety SENF2101 with a pesticidal composition. Pesticidal compositions include but are not limited to material that are insecticidal, fungicidal, detrimental to pathogens, or sometimes herbicidal.

"Variety" refers to a substantially homozygous soybean line and minor modifications thereof that retains the overall genetics of the soybean line including but not limited to a subline, a locus conversion, a mutation, a transgenic, or a somaclonal variant. Variety includes seeds, plants, plant parts, and/or seed parts of the instant soybean variety.

A description of the physiological and morphological characteristics of soybean plant variety SENF2101 is presented in Table 1. Characteristics reported are average values for all field trial locations and all years measured.

Soybean variety SENF2101 is uniform for breeding purposes and testing. Soybean variety SENF2101, being sufficiently homozygous, can be reproduced by planting seeds of the variety, growing resulting plants of the variety under self-pollinating or sib-pollinating conditions, and harvesting the resulting seed. Soybean variety SENF2101 shows no variants other than what would normally be expected by soybean breeders due to environment or to multiplication and repeated sexual reproduction.

The values presented for the characteristics identified in Table 1 are typical values. Some of these values may vary due to the environment and accordingly, other values that are substantially equivalent are also within the scope of the disclosure.

Provided is a soybean plant characterized by molecular and physiological data obtained from the representative sample of soybean variety SENF2101 deposited with the American Type Culture Collection. Thus, plants, seeds, or other parts thereof, having all or substantially all of the physiological, morphological, and/or phenotypic characteristics of soybean variety SENF2101 are provided. Further provided is a soybean plant formed by the combination of the disclosed soybean plant or plant cell with another soybean plant or cell and including the homozygous alleles of the variety. A soybean plant including all of the physiological, morphological and/or phenotypic characteristics of soybean variety SENF2101 can be combined with another soybean plant in a soybean breeding program. The other soybean plant may include all of the physiological, morphological and/or phenotypic characteristics of soybean variety SENF2101.

Soybean varieties such as SENF2101 are typically developed for use in seed and grain production. However, soybean varieties such as SENF2101 also provide a source of breeding material that may be used to develop new soybean varieties. Plant breeding techniques known in the art and used in a soybean plant breeding program include, but are not limited to, selfing, sibbing, recurrent selection, mass selection, bulk selection, backcrossing, pedigree breeding, sublining, open pollination breeding, crossing to populations, restriction fragment length polymorphism enhanced selection, genetic marker enhanced selection, predictive breeding, hybrid production, making double haploids, transformation, and gene editing. Often combinations of these techniques are used.

One goal of soybean breeders is to develop varieties with enhanced yield characteristics. Enhanced yield characteristics may include one or more of the following: increased germination efficiency under normal and/or stress conditions, improved plant physiology, growth and/or development, such as water use efficiency, water retention efficiency, improved nitrogen use, enhanced carbon assimilation, improved photosynthesis, and accelerated maturation, and improved disease and/or pathogen tolerance. Yield characteristics can furthermore include enhanced plant architecture (under stress and non-stress conditions), including but not limited to early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield characteristics include seed composition, such as carbohydrate content, protein content, oil content and composition, nutritional value, reduction in anti-nutritional compounds, improved processability, and better storage stability. The development of soybean varieties in a plant breeding program requires, in general, the development and evaluation of homozygous varieties. Many analytical methods exist and are available to those skilled in the art to evaluate a new variety. The oldest and most traditional method of analysis is the observation of phenotypic characteristics but genotypic analysis may also be used.

Methods for producing a soybean plant by crossing a first parent soybean plant with a second parent soybean plant where the first and/or second parent soybean plant is variety SENF2101 are provided. A method of producing hybrid soybean seeds is provided by crossing the soybean variety SENF2101 with a second, distinct soybean plant that is nonisogenic to soybean variety SENF2101. In particular embodiments of the disclosure, the crossing includes the steps of a) planting seeds of soybean variety SENF2101 and a second, distinct soybean plant, b) cultivating the soybean plants grown from the seeds until the plants bear flowers; c) cross-pollinating a flower on one of the two plants with the pollen of the other plant, and d) harvesting the seeds resulting from the cross-pollinating. Also provided are methods for producing a soybean plant having substantially all of the morphological and physiological characteristics of variety SENF2101, by crossing a first parent soybean plant with a second parent soybean plant where the first and/or the second parent soybean plant is a plant having substantially all of the morphological and physiological characteristics of variety SENF2101 set forth in Table 1, as determined at the 5% significance level when grown in the same environmental conditions. The other parent may be any soybean plant, such as a soybean plant that is part of a synthetic or natural population. Any such breeding methods using soybean variety SENF2101 may be used.

Pedigree breeding starts with crossing two genotypes, such as variety SENF2101 or a soybean variety having all of the morphological and physiological characteristics of variety SENF2101, and another soybean variety having one or more desirable characteristics that is lacking or that complements variety SENF2101. If the two original parents do not provide all the desired characteristics, other sources can be included in the breeding population. In the pedigree method, superior plants are selfed and selected in successive filial generations. In the succeeding filial generations, the heterozygous allele condition gives way to the homozygous allele condition as a result of inbreeding. Typically, in the pedigree method of breeding, five or more successive filial generations of selfing and selection are practiced: e.g., F1→F2; F2→F3; F3→F4; F4→F5; etc. In some examples, 1, 2, 3, 4, 5, 6, 7, 8, 9, 10, or more generations of selfing and selection are practiced. After a sufficient amount of inbreeding, successive filial generations serve to increase seed of the developed variety. Typically, the developed variety includes homozygous alleles at about 95% or more of its loci.

Sublines of soybean variety SENF2101 may also be developed and are provided. Although variety SENF2101 contains substantially fixed genetics and is phenotypically uniform with no off-types expected, there still remains a small proportion of segregating loci either within individuals or within the population as a whole. Sublining provides the ability to select for these loci, that have no apparent morphological or phenotypic effect on the plant characteristics, but may have an effect on overall yield. A breeder of ordinary skill in the art may fix agronomically relevant loci by making them homozygous to optimize the performance of the variety. The development of soybean sublines and the use of accelerated yield technology is a plant breeding technique.

Recurrent selection is a method used in a plant breeding program to improve a population of plants. Variety SENF2101 and a soybean variety having all of the morphological and physiological characteristics of SENF2101 are both suitable for use in a recurrent selection program. Individual plants are crossed with each other to form progeny. The progeny are grown and superior progeny are selected by any number of selection methods including individual plant, half-sib progeny, full-sib progeny, and selfed progeny. Selected progeny are cross pollinated with each other to form progeny for another population. This population is planted and, again, superior plants are selected to cross pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic cultivar. A synthetic cultivar is the resultant progeny formed by the intercrossing of several selected varieties.

Mass selection is a useful technique when used with molecular marker enhanced selection. In mass selection, seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk, and then using a sample of the seed harvested in bulk to plant the next generation. Also, instead of self-pollination, directed pollination could be used as part of the breeding program.

Mutation breeding is another method of introducing new traits into soybean variety SENF2101 or a soybean variety having all of the morphological and physiological characteristics of SENF2101. Any method of mutagenesis-creating a change in a nucleic acid of a plant, may be used with the disclosed variety, including the use of chemical mutagens (e.g. methanesulfonate, sodium azide, aminopurine, etc.), genome/gene editing techniques (e.g. CRISPR-like technologies, TALENs, zinc finger nucleases, and meganucleases), ionizing radiation (e.g. ultraviolet and/or gamma rays) temperature alterations, long-term seed storage, tissue culture conditions, targeting induced local lesions in a genome, sequence-targeted and/or random recombinases, etc. Mutations that occur spontaneously or that are artificially induced may be useful sources of variability for a plant breeder. The goal of artificial mutagenesis is to increase the rate of mutation for a desired characteristic. Once a desired trait is observed through mutagenesis, the trait may then be incorporated into existing germplasm by traditional breeding techniques. In addition, mutations created in other soybean plants may be used to produce a backcross conversion of SENF2101 that includes such mutation.

Molecular markers can also be used during the breeding process for the selection of qualitative traits. The use of molecular markers in the selection process is often called genetic marker enhanced selection. Markers closely linked to alleles or markers containing sequences within the actual alleles of interest can be used to select soybean plants that contain the alleles of interest during a backcrossing breeding program. The markers can also be used to select for the genome of the recurrent parent and against the genome of the donor parent to minimize the amount of genome from the donor parent that remains in the selected plants and to reduce the number of crosses back to the recurrent parent needed in a backcrossing program.

Doubled haploids are produced by the doubling of a set of chromosomes (IN) from a heterozygous plant to produce a completely homozygous individual. This can be advantageous because the process omits the generations of selfing needed to obtain a homozygous plant from a heterozygous source. The production of doubled haploids can also be used for the development of soybean plants with a homozygous phenotype in a breeding program. Soybean variety SENF2101 or a soybean variety having all of the phenotypic, morphological and/or physiological characteristics of variety SENF2101 as a parent can be used to produce doubled haploid plants.

A process for making a substantially homozygous SENF2101 progeny plant by producing or obtaining a seed from the cross of variety SENF2101 and another soybean plant and applying doubled haploid methods to the F1 seed or F1 plant or to any successive filial generation is provided. Such methods would decrease the number of generations required to produce a variety with similar genetics or characteristics to variety SENF2101.

In particular, a process of making seed retaining the molecular marker profile of soybean variety SENF2101 is contemplated. This can be accomplished by obtaining or producing F1 seed for which soybean variety SENF2101 is a parent, inducing doubled haploids to create progeny without the occurrence of meiotic segregation, obtaining the molecular marker profile of soybean variety SENF2101, and selecting progeny that retain the molecular marker profile of SENF2101.

Methods using seeds, plants, cells, or plant parts of variety SENF2101 in tissue culture such as to reproduce the variety are provided, as are the cultures, plants, parts, cells, and/or seeds derived therefrom. Tissue culture of various tissues of soybeans and regeneration of plants therefrom is well known and widely published. Thus, another aspect is to provide cells that upon growth and differentiation produce soybean plants having the physiological and morphological characteristics of soybean variety SENF2101.

In addition to phenotypic observations, a soybean plant can be identified by its genotype. The genotype of a plant can be characterized through a genetic marker profile that identifies plants of the same variety or a related variety, or that determines or validates a pedigree. Favorable genotypes and/or marker profiles, optionally associated with a trait of interest, may be identified by one or more methodologies known to those skilled in the art.

Molecular markers, including markers identified through the use of techniques such as isozyme electrophoresis, restriction fragment length polymorphisms (RFLPs), randomly amplified polymorphic DNAs (RAPDs), arbitrarily primed polymerase chain reaction (AP-PCR), DNA amplification fingerprinting (DAF), sequence characterized amplified regions (SCARs), amplified fragment length polymorphisms (AFLPs), simple sequence repeats (SSRs), single nucleotide polymorphisms (SNPs), and sequencing may be used in plant breeding methods utilizing variety SENF2101.

Methods are provided to characterize soybean variety SENF2101, or a variety including the phenotypic characteristics, morphological characteristics, physiological characteristics or combination thereof of soybean variety SENF2101. The methods can be used to produce nucleic acids from the plant, plant part, seed or plant cell, such nucleic acids can be, for example, analyzed by methods known to those skilled in the art, e.g., machine learning, to produce data. The data can be recorded and analyzed. The nucleic acids from the disrupted cell, the disrupted plant, plant part, plant cell or seed or the nucleic acids following isolation or separation can be contacted with primers and nucleotide bases, and/or a polymerase to facilitate PCR sequencing or marker analysis of the nucleic acids. In some embodiments, the nucleic acids produced can be sequenced or contacted with markers to produce a genetic profile, a molecular profile, a marker profile, a haplotype, or any combination thereof. The genetic profile or nucleotide sequence is recorded on a computer readable medium. The methods may further include using the nucleic acids produced from plants, plant parts, plant cells or seeds in a plant breeding program, for example in making soybean crossing, selection and/or advancement decisions in a predictive breeding program. Crossing includes any type of plant breeding crossing method, including but not limited to outcrossing, selfing, backcrossing, locus conversion, introgression, gene-editing, and the like.

In some embodiments, one or more markers are used to characterize and/or evaluate a soybean variety. Particular markers used for these purposes are not limited to any particular set of markers, but include any type of marker and marker profile that provides a means of distinguishing soybean varieties. One method of comparison is to use only homozygous loci for soybean variety SENF2101.

Primers and PCR protocols for assaying markers are disclosed in SoyBase that is available online. In addition to being used for identification of soybean variety SENF2101 and plant parts and plant cells of variety SENF2101, the genetic profile may be used to identify a soybean plant produced from variety SENF2101 as a germplasm source or to verify a pedigree for progeny plants produced through the use of SENF2101. The genetic marker profile is also useful in breeding and developing backcross conversions.

Means of performing genetic marker profiles using SSR polymorphisms are well known in the art. The SSR profile of soybean plant SENF2101 can be used to identify plants derived from SENF2101 as a parent, since such soybean plants include the same homozygous alleles as SENF2101. Because the soybean variety is essentially homozygous at all relevant loci, most loci should have only one type of allele present. In contrast, a genetic marker profile of an F1 progeny should be the sum of those parents, e.g., if one parent was homozygous for allele X at a particular locus, and the other parent homozygous for allele Y at that locus, then the F1 progeny will be XY (heterozygous) at that locus. Subsequent generations of progeny produced by selection and breeding are expected to be of genotype XX (homozygous), YY (homozygous), or XY (heterozygous) for that locus position. When the F1 plant is selfed or sibbed for successive filial generations, the locus should be either X or Y for that position.

In addition, plants and plant parts substantially benefiting from the use of soybean variety SENF2101 in their development, such as soybean variety SENF2101 including a backcross conversion, transgene, or genetic sterility factor, may be identified by having a molecular marker profile with a high percent identity to soybean variety SENF2101. Such a percent identity might be 90%, 91%, 92%, 93%, 94%, 95%, 96%, 97%, 98%, 99%, 99.5%, or 99.9% identical to soybean variety SENF2101.

The SSR profile of soybean variety SENF2101 also can be used to identify essentially derived varieties and other progeny varieties developed from the use of variety SENF2101, as well as cells and other plant parts thereof.

Plants include, for example, any plant having at least 90%, 91%, 92%, 93%, 94%, 95%, 96%, 97%, 98%, 99%, 99.5%, or 99.9% of the markers in the SSR profile, and that retain 90%, 91%, 92%, 93%, 94%, 95%, 96%, 97%, 98%, 99%, 99.5%, or 99.9% of the physiological and morphological characteristics of variety SENF2101 when grown under the same conditions. Progeny plants and plant parts produced using variety SENF2101 may be identified by having a molecular marker profile of at least 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 99.5% genetic contribution from soybean variety SENF2101, as measured by either percent identity or percent similarity. Such progeny may be further characterized as being within a pedigree distance of variety SENF2101, such as within 1, 2, 3, 4, or 5 or less cross-pollinations to a soybean plant other than variety SENF2101, or a plant that has variety SENF2101 as a progenitor. Unique molecular profiles may be identified with other molecular tools such as single nucleotide polymorphisms and restriction fragment length polymorphisms.

In addition to being used to create backcross conversion populations, backcrossing can also be used in combination with pedigree breeding. Backcrossing can be used to transfer one or more specifically desirable traits from one variety (the donor parent) to a developed variety (the recurrent parent), that has good overall agronomic characteristics yet may lack one or more other desirable traits. However, the same procedure can be used to move the progeny toward the genotype of the recurrent parent but at the same time retain many components of the non-recurrent parent by stopping the backcrossing at an early stage and proceeding with selfing and selection. For example, a soybean variety may be crossed with another variety to produce a first generation progeny plant. The first generation progeny plant may then be backcrossed to one of its parent varieties to create a BC1F1. Progeny are selfed and selected so that the newly developed variety has many of the attributes of the recurrent parent and yet several of the desired attributes of the donor parent. This approach leverages the value and strengths of both parents for use in new soybean varieties.

Therefore, in some embodiments a method to make a backcross conversion of soybean variety SENF2101 is provided by crossing a plant of soybean variety SENF2101 or a soybean variety having all of the morphological and physiological characteristics of SENF2101 with a donor plant possessing a desired trait to introduce the desired trait, selecting an F1 progeny plant containing the desired trait, and backcrossing the selected F1 progeny plant to a plant of soybean variety SENF2101 are provided. This method may further include the step of obtaining a molecular marker profile of soybean variety SENF2101 and using the molecular marker profile to select for a progeny plant with the desired trait and the molecular marker profile of SENF2101. The molecular marker profile may include information from one or more markers. In one example the desired trait is a mutant gene or transgene present in the donor parent. In another example, the desired trait is a native trait in the donor parent.

SSR technology is an efficient and practical marker technology; more marker loci can be routinely used and more alleles per marker locus can be found using SSRs in comparison to RFLPs. Single nucleotide polymorphisms (SNPs) may also be used to identify the unique genetic composition of variety SENF2101 and progeny varieties retaining or derived from that unique genetic composition. Various molecular marker techniques may be used in combination to enhance overall resolution.

Soybean DNA molecular marker linkage maps have been rapidly constructed and widely implemented in genetic studies. Sequences and PCR conditions of SSR loci in soybean, as well as the most current genetic map, may be found in the Soybase database available online.

One use of molecular markers is quantitative trait loci (QTL) mapping. QTL mapping is the use of markers that are known to be closely linked to alleles that have measurable effects on a quantitative trait. Selection in the breeding process is based upon the accumulation of markers linked to the positive effecting alleles and/or the elimination of the markers linked to the negative effecting alleles from the plant genome.

Variety SENF2101 represents a new genetic variety into which a locus or trait may be introduced or introgressed. Transformation, backcrossing and combinations thereof, represent methods that can be used to accomplish such an introgression.

Provided are soybean plants further including a locus conversion which plant may otherwise include, express or have all or essentially all of the morphological and physiological characteristics of the soybean variety SENF2101. In certain embodiments, the soybean plant includes a single locus conversion. The converted soybean plant may otherwise include, express or have all or essentially all of the morphological and physiological characteristics of the soybean variety SENF2101. By all or essentially all of the morphological and physiological characteristics, it is meant that all of the characteristics of a plant are recovered that are otherwise present when compared in the same environment, other than an occasional variant trait that might arise during backcrossing, or direct introduction of a transgene or a specific genetic modification.

In certain embodiments, the single locus conversion may include a transgenic gene that has been introduced by genetic transformation into the soybean variety SENF2101 or a progenitor thereof. In certain embodiments, the single locus conversion may include a dominant or recessive allele. The locus conversion may confer potentially any trait upon the single locus converted plant, including herbicide resistance, insect resistance, resistance to bacterial, fungal, or viral disease, male fertility or sterility, and improved nutritional quality.

It is known to those of skill in the art that, by way of the technique of backcrossing, one or more traits may be introduced into a given variety while otherwise retaining essentially all of the traits of that variety. A backcross conversion of variety SENF2101 occurs when DNA sequences are introduced through backcrossing with variety SENF2101 utilized as the recurrent parent. Naturally occurring, modified and transgenic DNA sequences may be introduced through backcrossing techniques. A backcross conversion may produce a plant with a trait or locus conversion in at least two or more backcrosses, including at least 2 backcrosses, at least 3 backcrosses, at least 4 backcrosses, at least 5 backcrosses, at least 6 backcrosses or more, depending at least in part on the differences between the parents of the original cross. Molecular marker assisted breeding or selection may be utilized to reduce the number of backcrosses necessary to achieve the backcross conversion.

The complexity of the backcross conversion method depends on the type of trait being transferred (a single gene or closely linked genes compared to unlinked genes), the level of expression of the trait, the type of inheritance (cytoplasmic or nuclear), dominant or recessive trait expression, and the types of parents included in the cross. It is understood by those of ordinary skill in the art that for single gene traits that are relatively easy to classify, the backcross method is effective and relatively easy to manage. Desired traits that may be transferred through backcross conversion include, but are not limited to, sterility (nuclear and cytoplasmic), fertility restoration, nutritional enhancements, drought tolerance, nitrogen utilization, altered fatty acid profile, low phytate, industrial enhancements, disease resistance (bacterial, fungal, or viral), insect resistance, and herbicide resistance. In addition, a recombination site itself, such as an FRT site, Lox site, or other site specific integration site, may be inserted by backcrossing and utilized for direct insertion of one or more genes of interest into a specific plant variety. A single locus conversion may contain several transgenes or modifications, such as a transgene or modification for disease resistance and for herbicide resistance. The gene for herbicide resistance may be used as a selectable marker and/or as a phenotypic trait. A single locus conversion of site specific integration system allows for the integration of multiple genes at a known recombination site in the genome. At least one, at least two or at least three and less than ten, less than nine, less than eight, less than seven, less than six, less than five or less than four locus conversions may be introduced into the plant by backcrossing, introgression or transformation to express the desired trait, while the plant, or a plant grown from the seed, plant part or plant cell, otherwise retains the phenotypic characteristics of the deposited seed when grown under the same environmental conditions.

The backcross conversion may result from either the transfer of a dominant allele or a recessive allele. Selection of progeny containing the trait of interest can be accomplished by direct selection for a trait associated with a dominant allele. Transgenes transferred via backcrossing typically function as a dominant single gene trait and are relatively easy to classify. Selection of progeny for a trait that is transferred via a recessive allele requires growing and selfing the first backcross generation to determine which plants carry the recessive alleles. Recessive traits may require additional progeny testing in successive backcross generations to determine the presence of the locus of interest. The last backcross generation is usually selfed to give pure breeding progeny for the trait(s) being transferred, although a backcross conversion with a stably introgressed trait may also be maintained by further backcrossing to the recurrent parent with subsequent selection for the trait.

Along with selection for the trait of interest, progeny are selected for the phenotype of the recurrent parent. The backcross is a form of inbreeding, and the features of the recurrent parent are recovered after successive backcrosses, such as at least one, at least two, at least three, at least 4 or at least 5 backcrosses. The number of backcrosses necessary can be reduced with the use of molecular markers. Other factors, such as a genetically similar donor parent, may also reduce the number of backcrosses necessary. Backcrossing is easiest for simply inherited, dominant, and easily recognized traits.

One process for adding or modifying a trait or locus in soybean variety SENF2101 includes crossing SENF2101 plants grown from SENF2101 seed with plants of another soybean variety that includes a desired trait lacking in SENF2101, selecting F1 progeny plants that possess the desired trait or locus to produce selected F1 progeny plants, crossing the selected progeny plants back to SENF2101 plants to produce backcross) (BC1) progeny plants. The BC1F1 progeny plants that have the desired trait and the morphological characteristics of soybean variety SENF2101 are selected and backcrossed to SENF2101 to generate BC2F1 progeny plants. Additional backcrossing and selection of progeny plants with the desired trait will produce BC3F1, BC4F1, BC5F1, . . . . BCxF1 generations of plants. The backcross populations of SENF2101 may be further characterized as having the phenotypic, physiological and/or morphological characteristics of soybean variety SENF2101, such as listed in Table 1, as determined at the 5% significance level when grown in the same environmental conditions and/or may be characterized by percent similarity or identity to SENF2101 as determined by SSR or other molecular markers. The above method may be utilized with fewer backcrosses in appropriate situations, such as when the donor parent is highly related or molecular markers are used in one or more selection steps. Desired traits that may be used include those nucleic acids known in the art that will affect traits through nucleic acid expression or inhibition. Desired loci also include the introgression of FRT, Lox, and/or other recombination sites for site specific integration. Desired loci further include QTLs that may also affect a desired trait.

In addition, the above process and other similar processes may be used to produce first generation progeny soybean seed by adding a step at the end of the process that includes crossing variety SENF2101 with the introgressed trait or locus with a different soybean plant and harvesting the resultant first generation progeny soybean seed.

Transgenes and transformation methods also provide means to engineer the genome of plants to contain and to express heterologous genetic elements, including but not limited to foreign genetic elements, additional copies of endogenous elements, and/or modified versions of native or endogenous genetic elements, to alter at least one trait of a plant in a specific manner. Any heterologous DNA sequence(s), whether from a different species or from the same species, that are inserted into the genome using transformation, backcrossing, or other methods known to one of skill in the art are referred to collectively as transgenes. The sequences are heterologous based on sequence source, location of integration, operably linked elements, or any combination thereof. One or more transgenes of interest can be introduced into soybean variety SENF2101. Transgenic variants of soybean variety SENF2101 plants, seeds, cells, and parts thereof or derived therefrom are provided. Transgenic variants of SENF2101 include the physiological and morphological characteristics of soybean variety SENF2101, such as listed in Table 1 as determined at the 5% significance level when grown in the same environmental conditions, and/or may be characterized or identified by percent similarity or identity to SENF2101 as determined by SSR or other molecular markers. In some examples, transgenic variants of soybean variety SENF2101 are produced by introducing at least one transgene of interest into soybean variety SENF2101 by transforming SENF2101 with a polynucleotide including the transgene of interest. In other examples, transgenic variants of soybean variety SENF2101 are produced by introducing at least one transgene by introgressing the transgene into soybean variety SENF2101 by crossing.

In one embodiment, a process for modifying soybean variety SENF2101 with the addition of a desired trait is provided, by transforming a soybean plant of variety SENF2101 with a transgene that confers a desired trait. Therefore, transgenic SENF2101 soybean cells, plants, plant parts, and seeds produced from this process are provided.

One or more desired traits may include traits such as herbicide resistance, insect resistance, disease resistance, decreased phytate, modified fatty acid profile, modified fatty acid content, carbohydrate metabolism, protein content, or oil content. Specific genes are known in the art and, include but are not limited to a polynucleotide conferring resistance to an ALS-inhibitor herbicide, imidazolinone, sulfonylurea, glyphosate, glufosinate, triazine, 2,4-dichlorophenoxyacetic acid (2,4-D), and dicamba herbicides; a polynucleotide encoding a *Bacillus thuringiensis* polypeptide, a polynucleotide encoding a phytase, a fatty acid desaturase (e.g., FAD-2, FAD-3), galactinol synthase, a raffinose synthetic enzyme; or a polynucleotide conferring resistance to soybean cyst nematode, brown stem rot, *Phytophthora* root rot, soybean mosaic virus, sudden death syndrome, or other plant pathogen.

In general, methods to transform, to modify, to edit or to alter soybean plant endogenous genomic DNA include altering the plant native DNA sequence or a pre-existing transgenic sequence including regulatory elements, coding and non-coding sequences. These methods can be used, for example, to target nucleic acids to pre-engineered target recognition sequences in the genome. Such pre-engineered target sequences may be introduced by genome editing or modification. A genetically modified plant variety may be generated using "custom" or engineered endonucleases. For example, site-specific modification of soybean plant genomes can also be performed using the bacterial type II CRISPR (clustered regularly interspaced short palindromic repeats)/Cas (CRISPR-associated) systems. The Cas/guide RNA-based system allows targeted cleavage of genomic DNA guided by a customizable small noncoding RNA in plants.

The modified soybean variety SENF2101 or a plant otherwise derived from variety SENF2101 may be further characterized as having all or essentially all of the phenotypic characteristics, or all or essentially all of the morphological and physiological characteristics of variety SENF2101, and/or may be characterized by percent identity to SENF2101 as determined by molecular markers, such as SSR markers or SNP markers. By essentially all of the phenotypic characteristics or morphological and physiological characteristics, it is meant that all of the characteristics of a plant are recovered that are otherwise present when compared in the same environment, other than an occasional variant trait that might arise during backcrossing or direct introduction of a transgene or specific genetic modification.

Plant transformation methods may involve the construction of an expression vector. Such a vector or recombinant construct includes a DNA sequence that contains a coding sequence, such as a protein and/or RNA coding sequence under the control of or operatively linked to a regulatory element, for example a promoter. The vector or construct may contain one or more coding sequences and one or more regulatory elements.

A genetic trait that has been engineered into the genome of a particular soybean plant may then be moved into the genome of another variety using traditional breeding techniques that are well known in the plant breeding arts. For example, a backcrossing approach is commonly used to move a transgene from a transformed soybean variety into an elite soybean variety, and the resulting backcross conversion plant would then contain the transgene(s).

Various genetic elements can be introduced into the plant genome using transformation. These elements include, but are not limited to, genes; coding sequences; inducible, constitutive, and tissue specific promoters; enhancing sequences; and signal and targeting sequences. The chromosomal location of the integrated DNA molecule may be determined.

Map information concerning chromosomal location is useful for proprietary protection of a subject transgenic plant. If unauthorized propagation is undertaken and crosses made with other germplasm, the map of the integration region can be compared to similar maps for suspect plants to determine if the latter have a common parentage with the subject plant.

Plants can be genetically engineered to express various phenotypes of agronomic interest. Through the transformation of soybean, the expression of genes can be altered to enhance disease resistance, insect resistance, herbicide resistance, agronomic, grain quality, and other traits. Transformation can also be used to insert DNA sequences that control or help control male-sterility. DNA sequences native to soybean as well as non-native DNA sequences can be transformed into soybean and used to alter levels of native or non-native proteins. Various promoters, targeting sequences, enhancing sequences, and other DNA sequences can be edited or inserted into the genome for the purpose of altering the expression of proteins. Reduction of the activity of specific genes (also known as gene silencing or gene suppression) is desirable for several aspects of genetic engineering in plants.

Exemplary nucleotide sequences and/or native loci that confer at least one trait of interest, that optionally may be conferred or altered by genetic engineering, transformation or introgression of a transformed event are well understood by those skilled in the art and include, but are not limited to, the following. 1. genes that confer resistance to insects or disease and that encode: (a) plant disease resistance genes, (b) a *Bacillus thuringiensis* (Bt) protein, a derivative thereof or a synthetic polypeptide modeled thereon, (c) antifungal genes, (d) genes conferring resistance to nematodes, (e) genes conferring resistance to *Phytophthora* Root Rot, and (f) genes that confer resistance to brown stem rot; 2. genes that confer resistance to a herbicide, for example: (a) a herbicide that inhibits the growing point or meristem, such as an imidazolinone, or a sulfonylurea, (b) glyphosate, (c) a herbicide that inhibits photosynthesis, such as a triazine and a benzonitrile, (d) genes that confer resistance to glufosinate containing herbicides, and (e) genes that confer resistance to dicamba; 3. genes that confer or contribute to a grain and/or seed characteristic, such as: (a) fatty acid profiles, (b) altered phosphate content, (c) altered carbohydrates, (d) altered antioxidant content or composition, (e) altered essential seed amino acids, and (f) altered amounts of protein and fatty acid in the seed; 4. genes that control male sterility; 5. polynucleotides including a sequence for site specific DNA recombination; and, 6. genes that affect abiotic stress resistance.

Seed cleaning refers to the removal of impurities and debris material from the harvested seed. Material to be removed from the seed includes but is not limited to soil, and plant waste, chaff, pebbles, weed seeds, broken soybean seeds, fungi, bacteria, insect material, including insect eggs, larvae, and parts thereof, and any other pests that exist with the harvested crop. Seed cleaning also refers to the removal of any debris or impurities such as low quality, infested, or infected seeds and seeds of different species that are foreign to the sample. Soybean seeds, plants, and plant parts of variety SENF2101 may be cleaned. Provided are methods to produce cleaned seed by cleaning a seed or a population or plurality of seeds. The resulting seeds, plants, or plant parts produced by the cleaning process(es) may exhibit enhanced yield characteristics.

Soybean seeds of variety SENF2101 may be treated. Provided are methods to produce treated seed by treating a seed or a population or a plurality of seeds. Treating a seed refers to the application of a composition to a seed as a coating or otherwise. The method can include a step of contacting the seed with a composition to coat the surface of the seed or to adhere the composition to the seed. The composition may be applied to the seed in a seed treatment at any time from harvesting of the seed to sowing of the seed. The composition may be applied using methods including but not limited to mixing in a container, mechanical application, tumbling, spraying, misting, and immersion. Thus, the composition may be applied as a powder, a crystalline, a ready-to-use, a slurry, a mist, and/or a soak. The composition to be used as a seed treatment may include one or more of a pesticide, a fungicide, an insecticide, a nematicide, an antimicrobial, an inoculant, a growth promoter, a polymer, a flow agent, a coating, or any combination thereof. In some embodiments, the seed treatment improves seed germination under normal and/or stress environments, early stand count, vigor, yield, root formation, nodulation, and any combination thereof. In some embodiments, seed treatment reduces seed dust levels, insect damage, pathogen establishment and/or damage, plant virus infection and/or damage, and any combination thereof.

Soybean seeds, plants, and plant parts of variety SENF2101 may be used or processed for food, animal feed, or a raw material(s) for industry. Seeds from variety SENF2101 can be crushed, or a component of the seeds can be extracted in order to make a plant product, such as protein concentrate, protein isolate, soybean hulls, meal, flour, or oil for a food or feed product. Methods of producing a plant product or a commodity product, such as protein concentrate, protein isolate, soybean hulls, meal, flour, or oil for a food or feed product by processing the plants, plant parts or grain are provided. Also provided are the protein concentrate, protein isolate, soybean hulls, meal, flour, or oil produced by the methods.

Soybean is also used as a food source for both animals and humans. Soybean is widely used as a source of protein for animal feeds for poultry, swine, and cattle, or specialty pet foods. For human consumption, soybean meal is made into soybean flour that is processed to protein concentrates used for meat extenders. Production of edible protein ingredients from soybean offers a healthy, less expensive replacement for animal protein in meats and dairy products. During processing of whole soybeans, the fibrous hull is removed and the oil is extracted. The remaining soybean meal is a combination of carbohydrates and approximately 50% protein.

Oil extracted from soybeans is used for cooking oil, margarine, and salad dressings. Soybean oil has a typical composition of 11% palmitic, 4% stearic, 25% oleic, 50% linoleic, and 9% linolenic fatty acid content. Fatty acid composition can be altered, for example, through transformation, breeding or a combination thereof, for improved oxidative stability and nutrition. For example, oleic acid can be raised to at least 70% or 75% of the total fatty acid content, and linolenic acid can be reduced to less than 5% or 3% of the total fatty acid content. Oil with 3% or less linolenic acid is classified as low linolenic oil, oil with less than 1% linolenic acid is classified as ultra-low linolenic oil. Oil with 70% or higher of oleic acid is classified as high oleic oil.

Industrial uses of soybean oil, that is typically subjected to further processing, include ingredients for paints, plastics, fibers, detergents, cosmetics, lubricants, and biodiesel fuel.

Soybean oil may be split, inter-esterified, sulfurized, epoxidized, polymerized, ethoxylated, or cleaved. To produce oil, the harvested soybeans are cracked, adjusted for moisture content, rolled into flakes, and then the oil is solvent-extracted. The oil extract is refined, optionally blended and/or hydrogenated. The mixture of triglycerides can be split and separated into pure fatty acids, that can be combined with petroleum-derived alcohols or acids, nitrogen, sulfonates, chlorine, or with fatty alcohols derived from fats and oils.

In addition to soybean meal, soybean can be used to produce soy flour. Soy flour refers to defatted soybeans where special care was taken during desolventizing to minimize protein denaturation and to retain a high nitrogen solubility index (NSI) in making the flour. Soy flour is the typical starting material for production of soy concentrate and soy protein isolate. Defatted soy flour is obtained from solvent extracted flakes and contains less than 1% oil. Full-fat soy flour is made from whole beans and contains about 18% to 20% oil. Low-fat soy flour is made by adding back some oil to defatted soy flour. The lipid content varies, but is usually between 4.5-9%. High-fat soy flour can also be produced by adding soybean oil to defatted flour at the level of 15%. Lecithinated soy flour is made by adding soybean lecithin to defatted, low-fat or high-fat soy flours to increase dispersibility and impart emulsifying properties.

For human consumption, soybean can be used to produce edible ingredients that serve as an alternative source of dietary protein. Common examples include milk, cheese, and meat substitutes. Additionally, soybean can be used to produce various types of fillers for meat and poultry products. Vitamins and/or minerals may be added to make soy products nutritionally more equivalent to animal protein sources as the protein quality is already roughly equivalent.

EMBODIMENTS

Various embodiments of the systems and methods provided herein are included in the following non-limiting list of embodiments.

1. A seed, plant, plant part, or plant cell of soybean variety SENF2101, representative seed of the variety having been deposited under ATCC Accession Number PTA-127286.
2. The seed of embodiment 1, that is free from transgenic events.
3. A method to produce a soybean seed, the method comprising the step of harvesting soybean seed from a cross of two soybean plants, where at least one soybean plant is the soybean plant of embodiment 1.
4. An F1 soybean seed produced by the method of embodiment 3.
5. A method to develop a second soybean plant, the method comprising the step of applying a plant breeding technique or a breeding tool to a plant grown from the seed of embodiment 3, where application of the technique results in development of the second soybean plant.
6. A method to produce a soybean plant derived from the variety SENF2101 comprising the steps of: a) crossing the soybean plant of embodiment 1 with itself or a second plant to produce progeny seed; b) growing the progeny seed to produce a progeny plant and crossing the progeny plant with itself or a different plant to produce further progeny seed; and, c) repeating step (b) for at least one additional generation to produce a soybean plant derived from the variety SENF2101.

7. A method comprising the step of isolating nucleic acids from the seed, plant, plant part, or plant cell of embodiment 1.

8 The method of embodiment 7, further comprising the steps of analyzing the nucleic acids to produce data and recording the data for soybean variety SENF2101.

9. The method of embodiment 8, wherein the data is recorded on a computer readable medium.

10. A method to edit the genome of soybean variety SENF2101, the method comprising the step of editing the genome of the seed, plant, plant part, or plant cell of embodiment 1, where the gene editing method is selected from the group selected from the group consisting of zinc finger nucleases, transcription activator-like effector nucleases (TALENs), engineered homing endonucleases/meganucleases, and clustered regularly interspaced short palindromic repeat (CRISPR)-associated protein systems.

11. A soybean seed or plant produced by the method of embodiment 10.

12. A soybean plant expressing all the physiological and morphological characteristics of the soybean plant of embodiment 1, representative seed of the variety having been deposited under ATCC Accession No. PTA-127286.

13. A method comprising the step of generating a molecular marker profile from nucleic acids isolated from the seed, plant, plant part, or plant cell of embodiment 1.

14. A method to produce a soybean seed or plant comprising a locus conversion, the method comprising the step of introducing the locus conversion into the seed or plant of embodiment 1.

15. A converted seed, plant, plant part or plant cell of soybean variety SENF2101, representative seed of the soybean variety SENF2101 having been deposited under ATCC Accession No. PTA-127286, where the converted seed, plant, plant part or plant cell comprises a single locus conversion, and where the plant or a plant grown from the converted seed, plant part or plant cell comprises the locus conversion and otherwise has the same morphological and physiological characteristics of soybean variety SENF2101 when grown under the same environmental conditions.

16. The converted seed, plant, plant part or plant cell of embodiment 15, where the single locus conversion confers a trait selected from the group consisting of male sterility, increased yield, a site-specific recombination site, abiotic stress tolerance, altered phosphate, altered antioxidants, altered fatty acids, altered essential amino acids, altered carbohydrates, herbicide resistance, insect resistance and disease resistance.

17. The converted seed, plant, plant part or plant cell of embodiment 15, where the locus conversion is introduced by backcrossing or transformation.

18. A method to produce treated seed, the method comprising the step of applying a seed treatment to the seed of embodiment 1.

19. A treated soybean seed produced by the method of embodiment 18.

20. A soybean commodity plant or seed produced from the plant or seed of embodiment 1, where the commodity plant product comprises as least one cell of soybean variety SENF2101.

EXAMPLES

Example 1

TABLE 1

Physiological and Morphological Characteristics of SENF2101 and Comparison Variety NINF1170

| Characteristic | SENF2101 | NINF1170 |
| --- | --- | --- |
| Seed coat color | Yellow | Yellow |
| Seed coat luster | Intermediate | Intermediate |
| Flower color | Purple | Purple |
| Hilum color | Brown | Brown |
| Plant pubescence color | Gray | Gray |
| Pod color | Brown | Brown |
| Plant habit | Indeterminate | Indeterminate |
| Plant height* | 90.1 | 88.4 |
| Maturity group | III | III |
| Relative maturity | 3.3 | 3.3 |
| Plant lodging | 2.0 | 1.6 |
| Seed yield | 58.5 | 61.9 |
| Shattering | 1 | 1 |
| Genetically modified herbicide resistance events | None | None |
| Leaflet Shape | Lanceolate | Ovate |
| Seeds per pod* | 2.41 | 2.31 |
| Seeds per pound | 3,215 | 2,981 |
| Pods per plant* | 73 | 48 |
| Seeds per plant | 115.7 | 99.8 |
| Seed size distribution | N | — |
| Seed oil content | 20.2 | 19.8 |
| Seed protein content | 43.7 | 43.4 |

*data from one location

Applicant has made a deposit of at least 625 seeds of Soybean Variety SENF2101 with the American Type Culture Collection (ATCC), 10801 University Boulevard, Manassas, VA 20110 USA, as ATCC Accession No. PTA-127286. The seeds deposited with the ATCC on Apr. 7, 2022, were taken from the seed stock maintained by Inari Agriculture, Inc., One Kendall Square, Building 600/700-Suite 7-501, Cambridge, MA 02139 since before the filing date of this application. Access to this seed stock will be available during the pendency of the application to the Commissioner of Patents and Trademarks and persons determined by the Commissioner to be entitled thereto upon request. All restrictions upon availability to the public will be irrevocably removed upon granting of the patent. The seed deposit of soybean variety SENF2101 will be maintained in the ATCC depository for a period of 30 years, or 5 years after the last request, or for the effective life of the patent, whichever is longer, and will be replaced if it becomes nonviable during that period.

All publications, patents, and patent applications mentioned in the specification are indicative of the level of those skilled in the art to which this disclosure pertains. All such publications, patents, and patent applications are incorporated by reference herein for the purpose cited to the same extent as if each was specifically and individually indicated to be incorporated by reference herein.

What is claimed is:

1. A seed, plant, plant part, or plant cell of soybean line SENF2101, representative seed of the line having been deposited under ATCC Accession Number PTA-127286.

2. The seed of claim 1.

3. A method to produce a soybean seed, comprising harvesting soybean seed from a cross of two soybean plants, where at least one soybean plant is the soybean plant of claim 1.

4. An F1 soybean seed produced by the method of claim 3.

5. A method to produce a soybean seed, comprising crossing a plant grown from the F1 seed of claim 4 with itself or a different plant and harvesting resulting seed.

6. A method to produce a soybean plant derived from the line SENF2101 comprising:

a) crossing the soybean plant of claim 1 with itself or a second plant to produce progeny seed;

b) growing the progeny seed to produce a progeny plant and crossing the progeny plant with itself or a different plant to produce further progeny seed; and, c) repeating step (b) for at least one additional generation to produce a soybean plant derived from the line SENF2101.

7. A method of isolating nucleic acids, comprising the step of isolating nucleic acids from the seed, plant, plant part, or plant cell of claim 1.

8. The method of claim 7, further comprising the steps of analyzing the nucleic acids to produce data and recording the data for soybean line SENF2101.

9. The method of claim 8, wherein the data is recorded on a computer readable medium.

10. A method of editing the genome of soybean line SENF2101 to introduce a desired trait, comprising editing the genome of the seed, plant, plant part, or plant cell of claim 1, thereby producing a gene edited SENF2101 seed, plant, plant part, or plant cell, respectively, where the gene editing method comprises use of zinc finger nucleases, transcription activator-like effector nucleases (TALENs), engineered homing endonucleases/meganucleases, or clustered regularly interspaced short palindromic repeat (CRISPR)-associated protein systems.

11. The gene edited SENF2101 seed, plant, plant part, or plant cell produced by the method of claim 10, where the gene edited SENF2101 seed, plant, plant part, or plant cell comprises the desired trait and otherwise all of the physiological and morphological characteristics of soybean line SENF 2101.

12. A soybean plant expressing all the physiological and morphological characteristics of the soybean plant of claim

1, representative seed of the line having been deposited under ATCC Accession No. PTA-127286.

13. A method comprising the step of generating a molecular marker profile from nucleic acids isolated from the seed, plant, plant part, or plant cell of claim 1.

14. A method to produce a soybean seed or plant comprising a locus conversion, comprising introducing the locus conversion into the seed or plant of claim 1.

15. A converted seed, plant, plant part, or plant cell of soybean line SENF2101, representative seed of the soybean line SENF2101 having been deposited under ATCC Accession No. PTA-127286, where the converted seed, plant, plant part, or plant cell comprises a single locus conversion, and where a plant grown from the converted seed, plant part, or plant cell comprises the locus conversion and otherwise has all of the morphological and physiological characteristics of soybean line SENF2101 when grown under the same environmental conditions.

16. The converted seed, plant, plant part, or plant cell of claim 15, where the single locus conversion confers a trait comprising male sterility, increased yield, a site-specific recombination site, abiotic stress tolerance, altered phosphate, altered antioxidants, altered fatty acids, altered essential amino acids, altered carbohydrates, herbicide resistance, insect resistance, or disease resistance.

17. The converted seed, plant, plant part, or plant cell of claim 15, where the locus conversion is introduced by backcrossing or transformation.

18. A method to produce treated seed, comprising applying a seed treatment to the seed of claim 1.

19. A treated soybean seed produced by the method of claim 18, where a soybean plant produced from the treated soybean seed has all of the physiological and morphological characteristics of soybean line SENF2101.

20. A soybean commodity plant or seed produced from the plant or seed of claim 1, where the commodity plant product comprises as least one cell of soybean line SENF2101.

\* \* \* \* \*